(12) United States Patent
Castro Pineiro et al.

(10) Patent No.: US 6,489,343 B2
(45) Date of Patent: Dec. 3, 2002

(54) TETRAHYDROPYRAN DERIVATIVES AND THEIR USE AS THERAPEUTIC AGENTS

(75) Inventors: Jose Luis Castro Pineiro, Bishops Stortford (GB); Simon Neil Owen, London (GB); Eileen Mary Seward, Bishops Stortford (GB); Christopher John Swain, Duxford (GB); Brian John Williams, Great Dunmow (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/933,064

(22) Filed: Aug. 20, 2001

(65) Prior Publication Data
US 2002/0035132 A1 Mar. 21, 2002

(30) Foreign Application Priority Data
Aug. 22, 2000 (GB) .............................................. 0020721

(51) Int. Cl.[7] ...................... A61K 31/445; C07D 211/60
(52) U.S. Cl. ........................ 514/326; 546/207; 549/416; 549/420
(58) Field of Search ................................ 549/416, 420; 546/207; 514/326

(56) References Cited

FOREIGN PATENT DOCUMENTS

| EP | 0 610 059 A | | 8/1994 |
| WO | WO 00/56727 | | 9/2000 |
| WO | WO 00/56728 | | 9/2000 |
| WO | WO 2000056727 | * | 9/2000 |
| WO | WO 2000056728 | * | 9/2000 |

OTHER PUBLICATIONS

A. Yamashita: *Tetrahedron Letters.*, vol. 29, No. 28, pp. 3403–3406 (1988).

* cited by examiner

*Primary Examiner*—Bernard Dentz
(74) *Attorney, Agent, or Firm*—J. Eric Thies; Melvin Winokur

(57) ABSTRACT

The present invention relates to compounds of the formula (I):

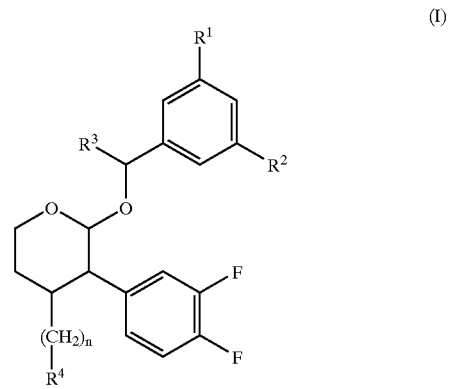

wherein $R^1$ is fluorine or trifluoromethyl;

$R^2$ is fluorine or trifluoromethyl;

$R^3$ is methyl or hydroxymethyl;

$R^4$ represents a variety of substituents; and n is zero, 1 or 2;

and pharmaceutically acceptable salts thereof.

The compounds are of particular use in the treatment or prevention of depression, anxiety, pain, inflammation, migaine, emesis or postherpetic neuralgia.

10 Claims, No Drawings

TETRAHYDROPYRAN DERIVATIVES AND THEIR USE AS THERAPEUTIC AGENTS

CROSS REFERENCE TO RELATED APPLICATIONS

This application claims priority under 35 U.S.C. §119 from GB Application No. 0020721.7 filed Aug. 22, 2000.

This invention relates to a class of tetrahydropyran compounds which are useful as tachykinin antagonists. More particularly, the compounds of the invention are useful as neurokinin 1 (NK-1) receptor antagonists.

By virtue of their excellent specificity for the human NK-1 receptor, the compounds of the present invention are particularly effective examples of this class of NK-1 receptor antagonist.

The present invention provides compounds of the formula (I):

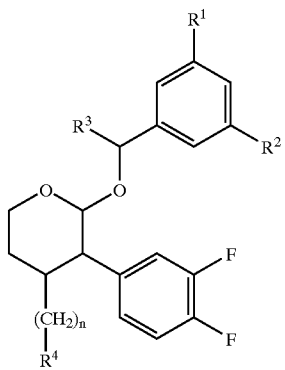

wherein $R^1$ is fluorine or trifluoromethyl;

$R^2$ is fluorine or trifluoromethyl;

$R^3$ is methyl or hydroxymethyl;

$R^3$ represents halogen, hydroxy, $C_{2-4}$alkenyl, $C_{2-4}$alynyl, $N_3$, —$NR^5R^6$, —$NR^aCOR^b$, —$OSO_2R^a$, —$(CH_2)_pNR^a(CH_2)_qCOOR^b$, $COR^a$, $COOR^a$, —N=C=O, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, $COR^a$, $CO_2R^a$, —$ZNR^5R^6$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, —$NR^5R^6$, —$NR^aCOR^b$, —$OSO_2R^a$, —$(CH_2)_pNR^a(CH_2)_qCOOR^b$, $COR^a$ or $COOR^a$;

$R^5$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^5$ is a five membered or six membered nitrogen-containing heteroaromatic ring as previously defined;

$R^6$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^5$, $R^6$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring, and said heteroaliphatic ring optionally containing a double bond, which heteroaliphatic ring may optionally contain an oxygen or sulphur ring atom, a group $S(O)$ or $S(O)_2$ or a second nitrogen atom which will be part of a NH or $NR^d$ moiety, where $R^d$ is $C_{1-4}$alkyl optionally substituted by hydroxy or $C_{1-4}$alkoxy, and where $R^e$ is hydrogen, $C_{1-4}$alkyl or benzyl;

or $R^5$, $R^6$ and the nitrogen atom to which they are attached form a non-aromatic azabicyclic ring system of 6 to 12 ring atoms;

or $R^5$, $R^6$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

Z represents a bond, $C_{1-6}$alkylene or $C_{3-6}$cycloalkylene;

n is zero, 1 or 2;

p is 1 or 2; and q is 1 or 2;

and pharmaceutically acceptable salts thereof.

A preferred class of compounds of formula (I) is that wherein $R^1$ is trifluoromethyl.

Another preferred class of compounds of formula (I) is that wherein $R^2$ is trifluoromethyl.

Also preferred is the class of compounds of formula (I) wherein $R^3$ is methyl.

Where —$NR^5R^6$ is defined as a substituent $R^4$ or as a substituent on a heteroaromatic ring in the definition of $R^4$, then $R^5$ may aptly be a $C_{1-4}$alkyl group or a $C_{2-4}$alkyl group substituted by a hydroxyl or $C_{1-2}$alkoxy group, $R^6$ may aptly be a $C_{1-4}$alkyl group or a $C_{2-4}$alkyl group substituted by a hydroxyl or $C_{1-2}$alkoxy group, or $R^5$ and $R^6$ may be linked so that, together with the nitrogen atom to which they are attached, they form an azetidinyl, pyrrolidinyl, piperidinyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group. Particularly preferred heteroaliphatic rings formed by —$NR^5R^6$ are azetidine, pyrolidine, piperidine, morpholine, piperazine and N-methylpiperazine, and especially piperidine.

Where the group $NR^5R^6$ represents a heteroaliphatic ring of 4 to 7 ring atoms substituted by two groups, the first substituent, where present, is preferably selected from hydroxy, $CO_2R^e$ (where $R^e$ is hydrogen, methyl, ethyl or benzyl), or $C_{1-2}$alkyl substituted by hydroxy. Where present, the second substituent is preferably a methyl group. Where two substituents are present, said substituents are preferably attached to the same carbon atom of the heteroaliphatic ring.

Where the group $NR^5R^6$ represents a heteroaliphatic ring of 4 to 7 ring atoms substituted by a spiro-fused lactone ring, particularly preferred examples are:

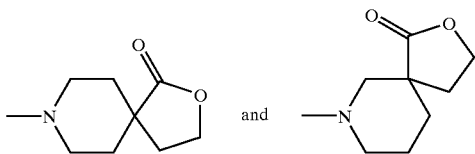

Where the group NR⁵R⁶ represents a heteroaliphatic ring of 4 to 7 ring atoms and said ring contains a double bond, a particularly preferred group is 3-pyrroline.

Where the group NR⁵R⁶ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where the group NR⁵R⁶ represents a heteroaliphatic ring of 4 to 7 ring atoms to which is fused a benzene ring or a five membered or six membered nitrogen-containing heteroaromatic ring ring optionally containing 1, 2 or 3 additional heteroatoms selected from N, O and S, said heteroaromatic ring is preferably a five-membered ring, in particular a pyrrole, imidazole or triazole ring, a nitrogen atom of which is preferably included in the heteroaliphatic ring. Suitable examples of such fused ring systems include

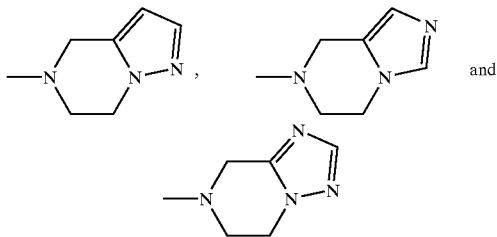

Particularly suitable moieties NR⁵R⁶ include those wherein NR⁵R⁶ is amino, methylamino, dimethylamino, diethylamino, azetidino, pyrrolidino, piperidino, morpholino and piperazino.

Where R⁴ represents an optionally substituted five or six-membered nitrogen-containing heteroaromatic ring optionally containing 1, 2 or 3 additional heteroatoms selected from N, O and S, the heteroaromatic ring is selected from pyrrole, pyridine, pyrazole, imidazole, oxazole, isoxazole, thiazole, isothiazole, pyrazine, pyrimidine, pyridazine, triazole, oxadiazole, thiadiazole, triazine, and tetrazole.

Preferred compounds of the present invention are those wherein R⁴ is a group selected from imidazole, 1,2,3-triazole and 1,2,4-triazole.

Particularly preferred compounds of the present invention are those wherein R⁴ is a group selected from imidazol-1-yl and 1,2,4-triazol-1-yl.

Where R⁴ represents an optionally substituted five membered or six membered nitrogen-containing heteroaromatic ring, preferred substituents are —ZNR⁵R⁶ and $C_{1-2}$alkyl (especially methyl). With reference to the group ZNR⁵R⁶ defined as a substituent on a heteroaromatic ring in the definition of R⁴, Z may be a bond or a linear, branched or cyclic group. Favourably Z is a bond or contains 1 to 4 carbon atoms and most favourably 1 to 2 carbon atoms. A particularly favourable group Z is —CH₂—. In this instance, particularly suitable moieties NR⁵R⁶ include those wherein NR⁵R⁶ is amino, methylamino, dimethylamino, diethylamino, azetidino, pyrrolidino, piperidino, morpholino and piperazino. Most especially, —ZNR⁵R⁶, as a substituent on a heteroaromatic ring in the definition of R⁴, is preferably CH₂N(CH₃)₂.

A further preferred class of compound of formula (I) is that wherein R⁴ represents halogen (especially iodine), hydroxy, vinyl, N₃ or OSO₂Rᵃ (especially where Rᵃ is methyl).

A further preferred class of compound of formula (I) is that wherein n is 1 or 2, and especially wherein n is 1.

One favoured group of compounds of the present invention are of the formula (Ia) and pharmaceutically acceptable salts thereof:

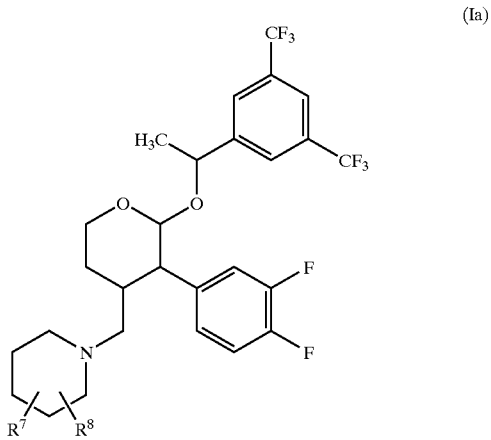

wherein

R⁷ and R⁸ each independently represent a group selected from hydrogen, hydroxy, CORᵉ, CO₂Rᵉ, $C_{1-4}$alkyl optionally substituted by a $C_{1-4}$alkoxy or hydroxy group, or a five membered nitrogen-containing heteroaromatic ring as previously defined;

or R⁷ or R⁸, where they are attached to the same carbon atom, may together form a spiro-fused lactone ring; and Rᵉ is hydrogen, $C_{1-4}$alkyl or benzyl.

Preferably R⁷ is selected from hydroxy, CORᵉ and CO₂Rᵉ.

Preferably R⁸ is selected from hydrogen, hydroxy and $C_{1-4}$alkyl.

More preferably, R⁷ is CO₂Rᵉ, where Rᵉ is, in particular, hydrogen, methyl or ethyl.

More preferably, R⁸ is methyl.

Most especially, R⁷ and R⁸ are attached to the same carbon atom, preferably at the para- or, more preferably, the meta-position on the piperidine ring.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-4}$alkyl" and "fluoro$C_{1-4}$alkoxy" means a $C_{1-4}$alkyl or $C_{1-4}$alkoxy group in which one or more (in particular, 1 to 3) hydrogen atoms have been replaced by fluorine atoms. Particularly preferred are fluoroC$_{1-3}$alkyl and fluoro$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:

cis, trans-(2R,3S,4R,8R)-2-[1-(3,5-bis(trifluoromethyl)phenyl)ethoxy]-3-(3,4-difluorophenyl)-4-vinyltetrahydropyran;

trans,trans-(2R,3R,4S,8R)-2-[1-(3,5-bis(trifluoromethyl)phenyl)ethoxy]-3-(3,4-difluorophenyl)-4-vinyltetrahydropyran;

(2R,3S,4S,8R)-2-[1-(3,5-bis(trifluoromethyl)phenyl)ethoxy]-3-(3,4-difluorophenyl)-tetrahydropyran-4-carbaldehyde;

(2R,3R,4R,8R, 10(3'R))-1-[2-[1-(3,5-Bis(trifluoromethyl)phenyl)ethoxy]-3-(3,4-difluorophenyl)-tetrahydropyran-4-ylmethyl]-3-methylpiperidine-3-carboxylic acid ethyl ester;

(2R,3R,4R,8R, 10(3'R))-[1-(2-1-(3,5-Bis(trifluoromethyl)phenyl)ethoxy1-3-(3,4-difluorophenyl)-tetrahydropyran-4-ylmethyl]-3-methylpiperidine-3-carboxylic acid;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, methanesulfonic acid, p-toluenesulfonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts. The methanesulfonate and p-toluenesulfonate salts are particularly preferred.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 2-, 3-, 4- and 8-positions as shown in formulae (Ib) and (Ic)

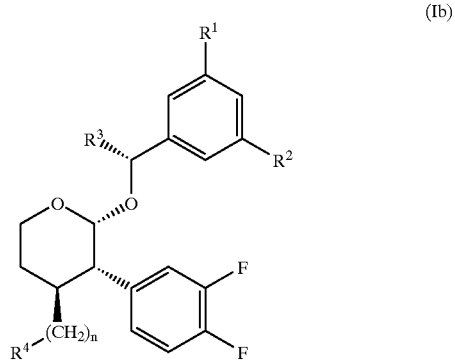

(Ib)

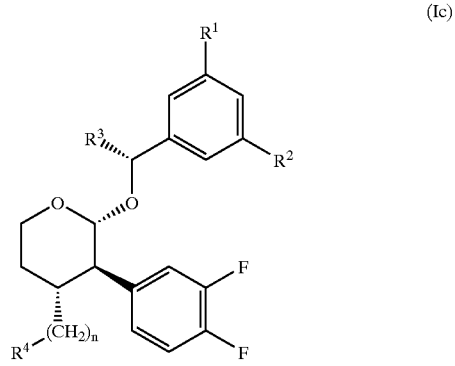

(Ic)

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, CreutzfeldtJakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and broncho-spasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

Tachykinin, including substance P, antagonists may also be of use in the treatment or prevention of pre-eclampsia (see Page et al, *Nature*, 405 (2000) 797–800).

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or domperidone or GABAB receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, $\alpha$-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676, WO 94/13677, WO 95/10506, WO 95/33750, WO 96/35689, WO 97/00868, WO 97/35539, WO 97/35580, WO 97/35846, WO 97/44038, WO 98/03510, WO 98/05661, WO 98/08846, WO 98/08847, WO 98/11075, WO 98/15543, WO 98/21200, WO 98/29413, WO 00/27846 and WO 00/27850.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"reatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The present invention is further directed to the use of a compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of formula (I) or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I), in which n is 1, may be prepared by the reaction of a compound of formula (II)

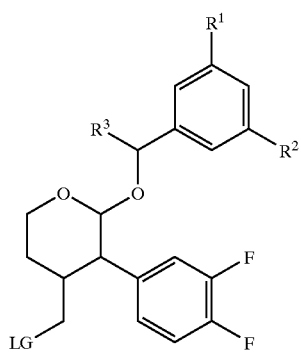

(II)

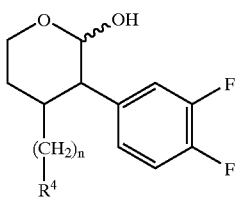

(IV)

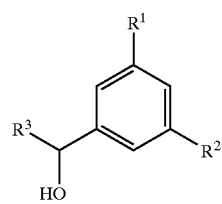

(V)

wherein LG is a suitable leaving group such as an alkyl- or arylsulfonyloxy group (e.g. mesylate or tosylate) or a halogen atom (e.g. bromine, chlorine or iodine); with an appropriate amine of the formula $HNR^5R^6$, or a heteroaromatic compound suitable for the addition of a five or six-membered nitrogen containing heteroaromatic ring as defined in relation to formula (I), or an azide such as sodium azide.

In each case, the reaction is preferably effected at an elevated temperature, for example, between 40° C. and 80° C., especially between 50° C. and 60° C. The reaction with a heteroaromatic compound is preferably effected in the presence of a suitable organic solvent such as dimethylformamide. The reaction with an azide is preferably effected in the presence of dimethylsulfoxide.

A particularly preferred compound of formula (II) is that wherein the group LG is mesylate—i.e. a compound of formula (I) in which $R^4$ is the group $—OSO_2CH_3$.

According to another general process (B), compounds of formula (I), in which $R^4$ is hydroxy and n is 1 or 2, may be prepared by the interconversion of a corresponding compound of formula (I) in which n is zero and $R^4$ is vinyl, hereinafter referred to as formula (III)

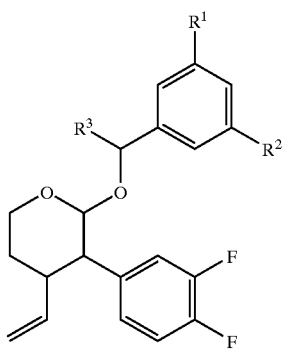

(III)

by reaction with ozone, followed by a reaction with a reducing agent such as sodium borohydride (n is 1), or by reaction with a reducing agent such as borane tetrahydrofuran complex, followed by hydrogen peroxidde in-the presence of a base such as sodium hydroxide.

According to another general process (C), compounds of formula (I) may be prepared by the reaction of a compound of formula (IV) with a compound of formula (V)

preferably in the presence of a resin catalyst such as Amberlyst™ 15, and 4 Angstrom molecular sieves.

The reaction is conveniently effected in a suitable solvent such as a halogenated hydrocarbon, for example, dichloromethane, conveniently at room temperature.

According to another general process (D), compounds of formula (I), in which $R^3$ is either methyl or hydroxymethyl, may be prepared by the reaction of a compound of formula (VI)

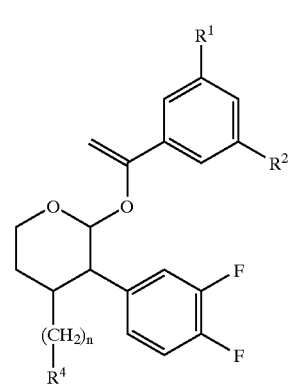

(VI)

wherein $R^{4a}$ is as defined for $R^4$ in relation to formula (I) or, more preferably, is a precursor therefor; under either:

(a) (where $R^3$ is methyl) catalytic hydrogenation conditions (e.g. $H_2$, $Pd(OH)_2$ on carbon) in a suitable solvent such as an ester, for example, ethyl acetate; or (b) (where $R^3$ is hydroxymethyl) reducing conditions (e.g. borane or $BH_3.THF$) followed by treatment with hydrogen peroxide and a base such as sodium hydroxide, conveniently in a solvent such as an ether, for example, tetrahydrofuran.

Where $R^{4a}$ is a precursor group (such as a TBDMS-protected hydroxyl group) deprotection is conveniently effected by treatment with an organic acid such as tetrabutylammonium fluoride.

According to another general process (E), compounds of formula (I), in which $R^4$ is $NR^5R^6$ and n is 1, may be prepared by the interconversion of a corresponding compound of formula (I) in which n is zero and $R^4$ is CHO, hereinafter referred to as formula (VII)

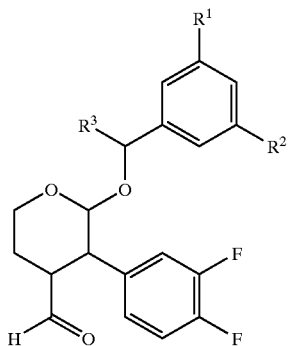

(VII)

by reaction with an amine of the formula HNR⁵R⁶, or salt thereof, in the presence of a reducing agent. Suitable reducing agents for the reductive amination of aldehiydes with primary or secondary amines are well known in the art. A particularly preferred reducing agent is sodium triacetoxyborohydride or sodium cyanoborohydride, in the presence of a base, such as a trialkylamine, for example, triethylamine.

Suitable bases for use in the reaction include organic bases, for example triethylamine.

The reaction is conveniently effected in an aprotic solvent such as a halogenated hydrocarbon, for example, dichloromethane.

Further details of suitable procedures will be found in the accompanying Examples.

Compounds of formula (II) may be prepared by conventional methods from, for example, a corresponding compound of formula (I) in which $R^4$ is a hydroxyl group. Thus, for example, when LG is a mesylate group a corresponding compound of formula (I) in which $R^4$ is hydroxyl may be reacted with methanesulfonyl chloride in the presence of a base, such as triethylamine. The reaction is conveniently effected in a solvent such as a halogenated hydrocarbon, for example, dichloromethane.

Compounds of formula (III) may be prepared, for example, by the method of general process (C), above.

Compounds of formula (IV) may be prepared by the reduction of a compound of formula (VIII)

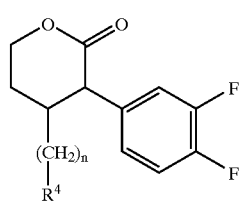

(VIII)

using conventional conditions such as sodium borohydride in the presence of a transition metal catalyst such as cerium chloride hexahydrate, in a solvent such as alcohol, for example, methanol or ethanol, or water or a mixture thereof; or using DiBAL in a solvent such as a halogenated hydrocarbon, for example, dichloromethane.

Compounds of formula (VIII) in which $R^4$ is vinyl, and n is zero may be prepared from the compound of formula (IX)

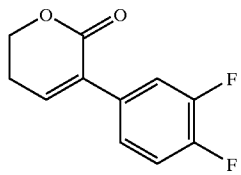

(IX)

by reaction with a vinyl Grignard reagent such as vinylMgBr or vinylMgCl, preferably in the presence of copper(I)iodide, and a suitable solvent such as an ether, for example, tetrahydrofuran. This reaction is effected at reduced temperature, for example, below −40° C. and preferably at −78° C.

Alternatively, compounds of formula (VIII) in which $R^4$ is vinyl and n is zero may be prepared by an intramolecular cyclisation reaction from the compound of formula (X)

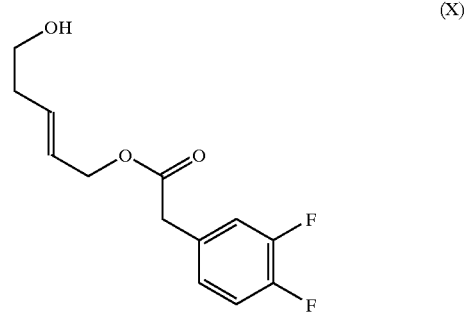

(X)

by reaction with trimethylsilyl trifluoromethanesulfonate in the presence of an organic base such as a trialkylamine, for example, triethylamine. The reaction is conveniently effected at a reduced temperature, such as at about 0° C., in the presence of an aprotic solvent such as a halogenated hydrocarbon, for example, dicbloromethane.

The compound of formula (X) may be prepared by the reaction of (E)-(R,S)-pent-2-en-1,5-diol, or more preferably, a protected derivative thereof, with 3,4-difluorophenylacetic acid under conventional conditions for preparing an ester from a carboxylic acid and an alcohol, such as in the presence of dimethylaminopyridine and 1-(3-dimethylaminopropyl)-3-ethylcarbodiimide. The reaction is conveniently effected in the presence of a trialkylamine, for example, triethylamine, and an aprotic solvent such as a halogenated hydrocarbon, for example dichloromethane.

The compound of formula (IX) may be prepared by the reaction of a 3-halo-5,6-dihydropyran-2-one (in particular where the halo is bromo) with 3,4-difluorophenylboronic acid. The reaction is conveniently effected under conditions well known in the art for such boronic acid coupling reactions, for instance, in the presence of a transition metal catalyst such as tetrakis(triphenylphosphine)palladium (0) and potassium fluoride, in a suitable solvent such as an ether, for example tetrahydrofuran. The reaction is preferably carried out in the presence of a base such as an alkali or alkaline earth metal carbonate, for example, potassium carbonate, at an elevated temperature, conveniently at the reflux temperature of the solvent.

Alternatively, the compound of formula (IX) may be prepared by a multi-step process as described in Description 9 of the accompanying Examples.

Compounds of formula (VI) may be prepared by the reaction of a compound of formula (XI)

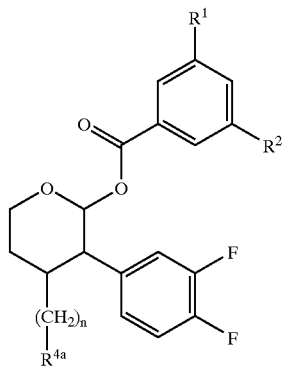

(XI)

with dimethyltitanocene in a solvent such as toluene, pyridine or tetrahydrofuran, or a mixture thereof.

Compounds of formula (XI) may be prepared by the reaction of a compound of formula (VIII) with L-Selectride™ (lithium tri-sec-butylborohydride) followed by treatment with a compound of formula (XII)

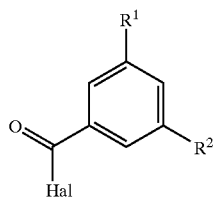

(XII)

wherein Hal is a halogen atom, preferably chlorine.

Compounds of formula (VII) may be prepared by the oxidation of a compound of formula (III) using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulphide liberates the desired aldehyde of formula (VII).

Compounds of formula (V) and (XII) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

(E)-(R,S)-5-(Tetrahydro-2H-pyran-2-yl)oxypent-2-en-1-ol *J. Med. Chem.* 1998, 41, 3972–3975

DESCRIPTION 2

(E)-(R,S)-(3,4-Difluorophenyl)acetic acid 5-(tetrahydropyran-2-yl)oxypent-2-enyl Ester To a stirred solution of the product from Description 1 (5.00g) in dichloromethane (110 ml) was added 3,4-difluorophenylacetic acid (5.54 g), triethylamine (11.2 ml), 4-dimethylaminopyridine (50 mg) and 1-(3-dimethylaminopropyl)-3-ethylcarbodiimide (7.71 g). After 16 hours, the reaction was quenched with 10 ml of saturated $NaHCO_3$ solution and extracted into ethyl acetate. The organic layer was washed with 10% citric acid solution and dried (brine, $MgSO_4$) before concentrating under reduced pressure to give a crude yellow oil. This was purified on silica eluting with 10–25% ethyl acetate/iso-hexane to afford the title compound as a pale yellow oil.

$^1$H NMR ($CDCl_3$, 400 MHz): δ 1.28–1.62 (6H, m), 1.68–1.74 (1H, m), 1.79–1.85 (1H, m) 2.34–2.39 (2H, m), 3.42–3.47 (1H, m), 3.48–3.53 (1H, m), 3.74–3.80 (1H, m), 3.82–3.88 (1H, m), 4.54–4.69 (3H, m), 5.60–5.67 (1H, m), 5.76–5.84 (1H, m), 6.96–6.99 (1H, m), 7.09–7.14 (2H, m).

DESCRIPTION 3

(3,4-Difluorophenyl)acetic acid 5-hydroxy-pent-2-enyl Ester

To a stirred solution of the product from Description 2 (100 mg) in ethanol (2.4 ml) was added pyridinium p-toluenesulphonate (7.4 mg) and the reaction heated to 55° C. for 75 minutes. The mixture was quenched with 1 ml of saturated $NaHCO_3$ solution and partitioned between ethyl acetate/water. The aqueous phase was extracted three times with ethyl acetate and the combined organic extracts were dried (brine, $MgSO_4$) before concentrating under reduced pressure to afford a crude colourless oil. This was purified on silica eluting with 15–25% ethyl acetate/iso-hexane to afford the title compound as a colourless oil.

$^1$H NMR ($CDCl_3$, 400 MHz): δ 2.33 (2H, q, J 6.5 Hz), 3.58 (2H, s), 3.68 (2H, t, J 9.8 Hz), 4.57 (2H, d, J 5.9 Hz), 5.63–5.80 (2H, m), 6.97–7.00 (1H, m), 7.07–7.15 (2H, m).

DESCRIPTION 4 cis/trans-3-(3,4-Difluorophenyl)-4-vinyl-tetrahydropyran-2-one

To a stirred solution of the product from Description 3 (4.60 g) and triethylamine (12.5 ml) in dichloromethane (30 ml) at 0° C. was added timethylsilyl trifluoromethanesulphonate (8.12 ml) in small portions. The cooling bath was removed and the reaction left for 64 hours. The resulting mixture was extracted into iso-hexane (×3) and the combined organics concentrated under reduced pressure to afford a crude brown oil. This oil was dissolved in methanol (150 ml), pyridinium p-toluenesulphonate (450 mg) added and the reaction stirred for 2 hours. The reaction mixture was concentrated under reduced pressure and azeotroped with toluene (×2) to afford a brown oil which was partitioned between ethyl acetate/50% saturated ammonium chloride solution. The organic phase was dried (brine, $MgSO_4$) and concentrated under reduced pressure to afford a brown oil which was taken up in toluene and refluxed in a Dean and Stark apparatus for 16 hours in the presence of additional pyridinium p-toluenesulphonate (450 mg). The reaction mixture was concentrated under *reduced pressure and partitioned between water/ethyl acetate. The organic phase was dried (brine, MgSO$_4$) and concentrated under reduced pressure to afford a crude brown oil which was purified on silica eluting with 15–30% ethyl acetate/iso-hexane to afford the title compound as a yellow oil. The ratio of diastereomers (cis:trans) was determined by $^1$H NMR as 1:6.

Signals for cis isomer: $^1$H NMR (CDCl$_3$, 400 MHz): δ 1.92–2.19 (2H, m), 2.92–2.99 (1H, m), 3.94 (1H, d, J 6.0 Hz), 4.42–4.63 (2H, m), 4.89–5.09 (2H, m), 5.50–5.64 (1H, m), 6.88–6.94 (1H, m), 6.97–7.07 (2H, m).

Signals for trans isomer: $^1$H NMR (CDCl$_3$, 400 MHz): δ 1.90–2.10 (1H, m), 2.12–2.19 (1H, m), 2.73–2.81 (1H, m), 3.45 (1H, d J 10.9 Hz), 4.43–4.57 (2H, m), 4.89–5.08 (2H, m), 5.55–5.64 (1H, m), 6.88–6.93 (1H, m), 6.98–7.03 (1H, m), 7.07–7.15 (1H, m).

DESCRIPTION 5 trans-3-(3,4-Difluorophenyl)-4-vinyl-tetrahydropyran-2-one

The product from Description 4 (2.93 g) was dissolved in 15 ml of tetrahydrofuran, 1,8-diazabicyclo[5.4.0]undec-7-ene (0.1 ml) added and the mixture refluxed for 5 minutes. The reaction was concentrated under reduced pressure to afford a brown oil which was purified on silica eluting with dichloromethane to afford the title compound as a colourless oil. The ratio of diastereomers (cis:trans) was determined by $^1$H NMR as 1:12.

Signals for trans isomer: $^1$H NMR (CDCl$_3$, 400 MHz): 5 1.90–2.10 (1H, m), 2.12–2.19 (1H, m), 2.73–2.81 (1H, m), 3.45 (1H, d J 10.9 Hz), 4.43–4.57 (2H, m), 4.89–5.08 (2H, m), 5.55–5.64 (1H, m), 6.88–6.93 (1H, m), 6.98–7.03 (1H, m), 7.07–7.15 (1H, m).

DESCRIPTION 6

3-(3,4-Difluorophenyl)-4-vinyl-tetrahydropyran-2-ol

The product from Description 5 was dissolved in ethanol (65 ml) and a solution of cerium trichloride heptahydrate (4.13 g) in 20 ml of water was added. The mixture was cooled to −20° C. before adding sodium borohydride (420 mg) in small portions. After 10 minutes, the reaction was quenched with 10 ml of acetone and allowed to warm to room temperature before concentrating under reduced pressure and partitioning between water/ethyl acetate. The aqueous phase was washed with further ethyl acetate and the combined organics dried (brine, MgSO$_4$) and concentrated under reduced pressure to afford a cloudy yellow oil. This was filtered through a Whatman 5 μm PTFE filter and azeotroped with toluene to afford the title compound as a yellow oil that crystallised on standing. Inspection by $^1$H NMR analysis revealed that this was a mixture of cis and trans isomers which was not purified further at this stage.

Signals for the cis isomer: $^1$H NMR (CDCl$_3$, 400 MHz): δ 1.55–1.80 (2H, m, H-5), 2.70 (1H, dd, J 11.9, 2.8 Hz, H-3), 2.91–3.00 (1H, m, H-4), 3.67–3.73 (1H, m, H-6$_{eq}$), 4.18 (1H, ddd, J 12.2, 2.8, 2.8, 2.8 Hz, H-6ax), 4.81–4.95 (2H, m, CH$_2$=CH), 5.15 (1H, d, J 2.9 Hz, H-2), 5.41–5.51 (1H, m, CH$_2$=CH), 6.87–7.20 (3H, m, ArH).

Signals for the trans isomer: $^1$H NMR (CDCl$_3$, 400 MHz): δ 1.55–1.80 (2H, m, H-5), 2.38 (1H, dd, J 11.4, 8.2 Hz, H-3), 2.45–2.52 (1H, m, H$_4$), 3.71 (1H, ddd, J 12.2, 2.8, 2.8 Hz, H-6$_{ax}$), 4.10–4.18 (1H, m, H-6$_{eq}$), 4.72 (1H, d, J 8.2 Hz, H-2), 4.81–4.95 (2H, m, CH$_2$=CH), 5.41–5.51 (1H, m, CH$_2$=CH), 6.87–7.20 (3H, m, ArH).

DESCRIPTION 7

3-(3,4-Difluorophenyl)-5,6-dihydropyran-2-one

A solution of 3-bromo-5,6-dihydropyran-2-one (87.4 g, 0.49mol), 3,4-difluorophenylboronic acid (91.4 g, 0.58 mol), potassium carbonate (99.9 g, 0.72 mol), potassium fluoride (85.4 g, 1.47 mol) and tetrakis(triphenylphosphine) palladium (0) (12 g, 0.01 mol) in tetrahydrofuran (600 ml) was thoroughly degassed and then heated at reflux for 48 hours under an atmosphere of nitrogen. The solution was cooled to room temperature and water (1000 ml) and ethyl acetate (1000 ml) were added. The organic phase was washed with saturated brine and dried (MgSO$_4$) and the solvent removed in vacuo. The residue was dissolved in dichloromethane and the solution filtered through a pad of silica gel. The filtrate was evaporated to dryness and the residue recrystallized from diethyl ether to give the title compound 34.6 g. mp 82–85° C. $^1$H NMR (360 MHz. CDCl$_3$) δ 2.63 (2H, td J 6.2 Hz and 4.5 Hz), 4.49 (2H, t J 6.3 Hz), 7.01 (1H, t J 4.5 Hz), 7.11–7.23 (2H, m), 7.32–7.38 (1H, m).

DESCRIPTION 8

3-(3,4-Difluorophenyl)-4-vinyl-tetrahydropyran-2-one (Alternative Preparation)

To a cooled (−78° C.) suspension of copper (I) iodide in tetrahydrofuran (152 ml) was added a solution of vinyl magnesium chloride (1.73M in tetrahydrofuran, 146 ml). After stirring the solution at −78° C. for 30 minutes a solution of the product of Description 7 (53.4 g) and chlorotrimethylsilane (32.3 ml) in tetrahydrofuran (250 ml) was slowly added such that the temperature of the solution remained below −60° C. After stirring the solution at −78° C. for 30 minutes additional vinyl magnesium chloride (1.73M in tetrahydrofuran, 20 ml) was added and the fixture stirred for 30 minutes. The cooled solution was then poured slowly onto saturated aqueous solution of ammonium chloride (1.5L). The organic phase as separated and evaporated to dryness. The residue was dissolved in ethyl acetate (1L) and this solution was washed with water, saturated brine and then dried (MgSO$_4$). Removal of the solvent in vacuo gave the title compound as a 3:1 cis:trans mixture of diastereomers. This residue was dissolved in tetrahydrofuran (200 ml) and 1,8-diazabicyclo[5.4.0]undec-7-ene (2.2 ml) was added and the solution heated under reflux for 1 hour. The solvent was removed from the cooled solution in vacuo and the residue dissolved in dichloromethane (200 ml). This solution was filtered through a bed of silica gel eluting with dichloromethane to give the title compound as a 1:25 cis:trans mixture of diastereomers (53.2 g).

$^1$H NMR (trans isomer, 360 MHz, CDCl$_3$) δ 1.90–2.01 (1H, m), 2.11–2.20 (1H, m), 2.72–2.81 (1H, m), 3.45 (1H, d J 10.9 Hz), 4.42–4.56 (2H, m), 4.90 (1H, d J 17.2 Hz), 5.05 (1H, d J 10.4 Hz), 5.61 (1H, m), 6.89 (1H, m), 7.00 (1H, m), 7.13 (1H, m).

DESCRIPTION 9

3-(3,4-Difluorophenyl)-5,6-dihydropyran-2-one (Alternative Preparation)

i) 3,4-Difluorophenylacetyl Chloride

To a heated (50° C.) solution of 3,4-difluorophenylacetic acid (45 g, 0.26 mol) and dimethylformamide (0.5 ml) in dichloromethane (150 ml) was slowly added (over 30 minutes) a solution of thionyl chloride (22.9 ml) in dichloromethane (50 ml). The solution was heated at 5° C. for a further 90 minutes. After cooling the solution the solvent was removed by evaporation in vacuo and any remaining thionyl chloride removed azeotropically by evaporation from a toluene solution. The residual oil (still containing toluene and dimethylformamide) was used without further purification NMR (360 MHz. CDCl$_3$) δ 4.09 (s), 6.96–7.27 (m, aryl and toluene signals), (additional signals from toluene 2.35 (s), and dimethylformamide 2.88 (s), 2.94 (s)).

ii) 3-Bromopropyl 3,4-difluorophenylacetatate

To a solution of the product of Description 9(i) in dichloromethane (200 ml) was added a solution of 3-bromopropan-1-ol (37.7 g) in dichloromethane (100 ml) and the mixture heated under reflux for 5 hours. The solution was cooled to room temperature and the solvent removed in vacuo to give an oil (88.4 g) which was used below without further purification.

$^1$H NMR (360 MHz. CDCl$_3$) δ 2.17 (2H, pent J 6.3 Hz), 3.41 (2H, t J 6.5 Hz), 3.59 (2H, s), 4.25 (2H, t J 6.1 Hz), 6.99 (1H, m), 7.07–7.15 (2H, m), (additional signals from dimethyl formamide at 2.88(s), 2.96(s).

iii) 3-(3,4-Difluorophenyl)-3,4,5,6-tetrahydropyran-2-one

To a heated (50° C.) suspension of sodium hydride (60% in mineral oil, 19.4 g) in tetrahydrofuran (1000 ml) was slowly added a solution of the product from Description 9(ii) (82 g) in tetrahydrofuran (300 ml) over 1.5 hours. After the addition was complete the solution was heated for a further 30 minutes at 5° C. The solution was cooled to room temperature and glacial acetic acid (20 ml) added dropwise and the solvent removed in vacuo. The residue was partitioned between ethyl acetate and water and the organic phase washed with saturated brine and dried (MgSO$_4$). After removal of the solvent in vacuo the residue was triturated with hexane (3 times) to give a sticky solid. The residue was precipitated from a solution in diethyl ether by addition of hexane and cooling the resultant solution to −20° C. to give the title compound as a pale yellow slightly sticky solid (43 g). An authentic sample of purified material could be obtained by distillation bp$_{1.5mm}$ 140° C. and crystallization from diethyl ether mp 66–69° C.

$^1$H NMR (400 MHz. CDCl$_3$) δ 1.97–2.09 (3H, m), 2.24–2.34 (1H, m), 3.71–3.75 (1H, m), 4.40–4.50 (2H, m), 6.95–6.99 (1H, m), 7.05–7.17 (2H, m).

iv) 3-Bromo-3-(3,4-difluorophenyl)-3,4,5,6-tetrahydropyran-2-one

A solution of the product of Description 9(iii) (43 g), N-bromosuccinimide (54 g) and benzoylperoxide (0.3 g) in carbon tetrachloride were heated under an atmosphere of nitrogen under reflux for 8 hours and then the solution was cooled to room temperature and filtered. The filtrate was evaporated in vacuo and used below without further purification.

NMR (360 MHz. CDCl$_3$) δ 1.89–1.96 (1H, m), 2.35–2.41 (1H, m), 2.61–2.77 (2H, m), 4.37–4.44 (1H, m), 4.58–4.64 (1H, m), 7.18 (1H, ddd J 8.6 Hz, 8.6 Hz and 9.3 Hz), 7.33–7.36 (1H, m), 7.50–7.56 (1H, m).

v) 3-(3,4-difluorophenyl)-5,6-dihydropyran-2-one

A suspension of the product of Description 9(iv), lithium bromide (25.8 g) and lithium carbonate (21.9 g) in tetrahydrofuran (550 ml) were heated under reflux for 2 hours. The solvent was removed in vacuo from the cooled solution and the residue partitioned between ethyl acetate and water. The organic phase was washed with saturated brine, dried (MgSO$_4$) and evaporated to dryness. The product was crystallized from diethyl ether with cooling (5° C.) to give the title compound (18.8 g) as a pale brown solid mp 72–78° C. A second crop (4.6 g) was obtained by crystallization of the mother liquors.

$^1$H NMR (360 MHz. CDCl$_3$) δ 2.63 (2H, td J 6.2 Hz and 4.5 Hz), 4.49 (2H, t J 6.3 Hz), 7.01 (1H, t J 4.5 Hz), 7.11–7.23 (2H, m), 7.32–7.38 (1H, m).

EXAMPLE 1 a) 5-(3,4-Difluorophenyl)-4-vinyl-3,4-dihydro-2H-pyran b) Cis-trans-(2R,3S,4R,8R)-2-[1-(3,5-Bis (trifluoromethyl)phenyl)ethoxy]-3-(3,4-difluorophenyl)-4-vinyltetrahydropyran c) Trans-trans-(2R,3R,4S,8R)-2-[1-(3,5-Bis (trifluoromethyl0phenyl)ethoxy]-3-(3,4-difluorophenyl)-4-vinyltetrahydropyran The product from Description 6 (2.70 g) and (R)-1-(3,5-Bis(trifluoromethyl)phenyl)ethanol (5.78 g) were dissolved in DCM (8.5 ml). Amberlyst-15 resin (1.5 g) and 4 Å molecular sieves (5.0 g) were added and the reaction mixture stirred for 30 minutes at room temperature before cooling to 4° C. and standing for 64 hours. The reaction was filtered and concentrated under reduced pressure to afford a crude yellow oil. This was purified on silica eluting with 0–25% dichloromethane/iso-hexane to afford the title compounds, respectively, as pale yellow oils.

a) Signals for enol ether: $^1$H NMR (CDCl$_3$, 400 MHz): δ 1.50–1.58 (1H, m), 1.80–1.84 (1H,m), 2.05–2.11 (1H, m), 3.27–3.31 (1H, m), 3.91 (1H, td, J 11.7, 2.3 Hz), 4.08–4.12 (1H, m), 4.96 (1H, dt, J 17.0, 1.3 Hz), 5.10 (1H, dt, J 10.3, 1.3 Hz), 5.80 (1H, ddd, J 17.0, 10.2, 6.3 Hz), 6.87 (1H, s), 6.95–6.99 (1H, m), 7.04–7.08 (1H, m).

b) Signals for cis-trans isomer (most non-polar diastereoisomer): $^1$H NMR (CDCl$_3$, 400 MHz): δ 1.47 (3H, d, J 6.5 Hz), 1.74 (1H, qd, J 12.6, 4.9 Hz), 1,81–1.84 (1H, m), 2.68 (1H, dd, J 11.9, 3.2 Hz), 2.98–3.09 (1H, m), 3.76 (1H, ddd, J 11.2, 4.9, 1.4 Hz), 4.04 (1H, td, J 11.5, 2.6 Hz), 4.44 (1H, d, J 3.2 Hz), 4.87–5.00 (3H, m), 5.41–5.50 (1H, m), 6.86–6.90 (1H, m), 7.02–7.09 (2H, m), 7.22 (1H, s), 7.64 (1H, s).

c) Signals for trans-trans isomer (most polar diastereoisomer): $^1$H NMR (CDCl$_3$, 400 MHz): δ 1.38 (3H, d, J 6.6 Hz), 1.67–1.71 (2H, m), 2.34–2.41 (1H, m), 2.48–2.52 (1H, m), 3.52–3.59 (1H, m), 4.11–4.16 (2H, m), 4.77–4.84 (2H, m), 4.97 (1H, q, J 6.6 Hz), 5.39–5.47 (1H, m), 6.73–6.77 (1H, m), 6.86–6.80 (1H, m), 7.00–7.06 (1H, m), 7.20 (2H, s), 7.70 (1H, s).

EXAMPLE 2

(2R,3R,4R,8R)-2-[1-(3,5-Bis(trifluoromethyl) phenyl)ethoxy]-3-(3,4-difluorophenyl) tetrahydropyran-4-carbaldehyde The product from Example 1c (1.40 g) was dissolved in a mixture of dichloromethane (30 ml) and methanol (15 ml) and cooled to −78° C. under a nitrogen atmosphere. Oxygen was then bubbled through the reaction, followed by ozone (until a blue colour developed), further oxygen and finally the reaction was purged with nitrogen. Dimethyl sulphide (5.35 ml) was then added and the reaction allowed to warm to room temperature. After stirring for 2 hours, the reaction was concentrated under reduced pressure, taken up in ethyl acetate, washed with water (×5) and dried (brine, MgSO₄). After concentrating under reduced pressure, the resulting colourless oil was purified on silica eluting with 10–25% ethyl acetate/iso-hexane to afford the title compound as a pale yellow oil.

$^1$H NMR (CDCl₃, 400 MHz): δ 1.41 (3H, d, J 6.6 Hz), 1.80–1.86 (2H, m), 2.69–2.74 (1H, m), 2.98–3.02 (1H, m), 3.57–3.63 (1H, m), 4.15–4.19 (1H, m), 4.26 (1H, d, J 7.2 Hz), 4.97 (1H, q, J 6.6 Hz), 6.89–6.62 (1H, m), 6.98–7.11 (2H, m), 7.29 (2H, s), 7.72 (1H, s), 9.49 (1H, s).

EXAMPLE 3

(2R,3R,4R,8R,10(3')R)-1-[2-[1-(3,5-Bis(trifluoromethyl)phenyl)ethoxy]-3-(3,4-difluorophenyl)tetrahydropyran-4-yl)methyl]-3-methylpiperidine-3-arboxylic Acid Ethyl Ester The product from Example 2 (150 mg) was dissolved in 1,2-dichloroethane (2 ml) and (R)-3-methylpiperidine-3-carboxylic acid ethyl ester hemi-dibenzoyl-D-artrate salt (217 mg) was added. Triethylamine (86 μl) and sodium riacetoxyborohydride (131 mg) were added and the reaction stirred for 16 hours at room temperature. The reaction was quenched with 1 ml of saturated NaHCO₃ solution and extracted into dichloromethane. The organic phase was dried (brine, MgSO₄) and concentrated under reduced pressure to afford a colourless oil which was purified on silica eluting with 5–15% ethyl acetate/iso-hexane to afford a colourless oil which crystallised on standing.

$^1$H NMR (CDCl₃, 400 MHz): δ 1.07 (3H, s), 1.24 (3H, t, J 7.2 Hz), 1.31–1.42 (4H, m), 1.43–1.60 (3H, m), 1.71–1.96 (7H, m), 2.33–2.40 (2H, m), 2.64–2.70 (1H, m), 3.48 (1H, td, J 12.2, 2.0 Hz), 4.06–4.14 (4H, m), 4.95 (1H, q, J 6.6 Hz), 6.74–6.77 (1H, m), 6.84 (1H, ddd, J 11.2, 7.6, 2.0 Hz), 6.70–7.06 (1H, m), 7.19 (2H, s), 7.69 (1H, s). MS (ES+) m/z 638 (M+1, 100%), 380 (M-258, 70%)

EXAMPLE 4

(2R,3R,4R,8R,10(3)R)-1-[2-[1-(3,5-Bis(trifluoromethyl)phenyl)ethoxy]-3-(3,4-difluorophenyl)tetrahydropyran-4-ylmethyl]-3-methylpiperidine-3-carboxylic Acid The product from Example 3 (146 mg) was dissolved in methanol (20 ml), 4M sodium hydroxide added (5 ml) and the reaction stirred at 65° C. for 16 hours. The reaction was concentrated under reduced pressure, partitioned between ethyl acetate/water and the aqueous phase brought to pH-6.5 with 2M hydrochloric acid. The aqueous phase was extracted into ethyl acetate (×3) and the combined organics dried (brine, MgSO₄) and concentrated under reduced pressure to afford a yellow oil. This was purified on silica eluting with 0–10% methanol/dichloromethane to afford the title compound as a white amorphous powder. This was crystallised from ether to afford the title compound as a white crystalline solid.

$^1$H NMR (CDCl₃, 400 MHz): δ 1.11 (3H, s, CH₃), 1.10–1.17 (1H, m), 1.38 (3H, d, J 6.6 Hz, CH₃), 1.50 (1H, dddd, J 13.2, 4.4, 4.4, 4.4 Hz, H-5), 1.62–1.76 (3H, m), 1.88–1.92 (2H, m), 1.98–2.05 (2H, m), 2.10 (1H, dd, J 12.6, 2.9 Hz), 2.20 (1H, dd, J 12.6, 11.1 Hz), 2.37 (1H, dd, J 11.3, 8.3 Hz), 2.77 (1H, d, J 11.7 Hz), 2.89–2.91 (1H, br d), 3.54 (1H, ddd, J 12.1, 2.0, 2.0 Hz, H-6$_{ax}$), 4.12 (1H, d, J 8.3 Hz, H-2), 4.17 (1H, dd, J 12.0, 3.2 Hz, H-6$_{eq}$), 4.97 (1H, q, J 6.6 Hz), 6.76 (1H, m), 6.82–6.87 (1H, m), 7.08 (1H, q, J 8.4 Hz), 7.19 (2H, s), 7.70 (1H, s). MS (ES+) m/z 610 (m+1, 100%), 352 (m-258, 45%)

What is claimed is:

1. A compound of the formula (Ia):

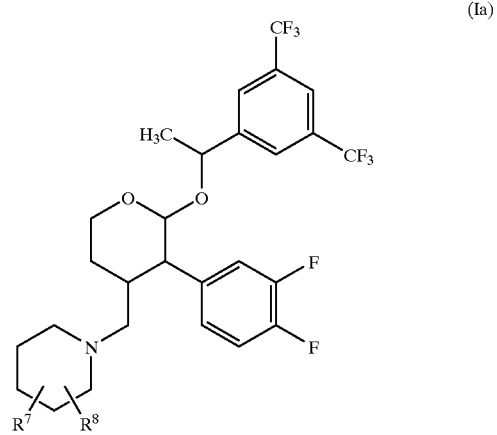

wherein

R⁷ is selected from hydroxy, COR$^e$ and CO₂R$^e$;

R⁸ is selected from hydrogen, hydroxy and C$_{1-4}$alkyl; and

R$^e$ is hydrogen, C$_{1-4}$alkyl or benzyl;

or a pharmaceutically acceptable salt thereof.

2. A compound as claimed in claim 1 wherein R⁷ is CO₂R$^e$, where R$^e$ is hydrogen, methyl or ethyl.

3. A compound which is:

(2R,3R,4R,8R,10(3'R))-1-[2-[1-(3,5-bis(trifluoromethyl)phenyl)ethoxy]-3-(3,4-difluorophenyl)-tetrahydropyran-4-ylmethyl]-3-methylpiperidine-3-carboxylic acid ethyl ester;

or a pharmaceutically acceptable salt thereof.

4. A compound as claimed in claim 1 wherein R⁸ is methyl.

5. A compound as claimed in claim 1 wherein R⁷ and R⁸ are both attached to the carbon atom at the meta- position on the piperidine ring.

6. A compound which is:

(2R,3R,4R,8R,10(3'R))-1[2-[1-(3,5-bis(trifluoromethyl)phenyl)ethoxy]-3-(3,4-difluorophenyl)-tetrahydropyran-4-ylmethyl]-3-methylpiperidine-3-carboxylic acid;

or a pharmaceutically acceptable salt thereof.

7. A pharmaceutical composition comprising a compound as claimed in any claim 1, together with at least one pharmaceutically acceptable carrier or excipient.

8. A method for the treatment or prevention of physiological disorders associated with an excess of tachykinins, which method comprises administration to a patient in need thereof of a tachykinin reducing amount of a compound according to claim 1.

9. A method for the treatment or prevention of pain or inflammation, migraine, emesis, postherpetic neuralgia, depression or anxiety, which method comprises administration to a patient in need thereof of a therapeutically effective amount of a compound according to claim 1.

10. A process for the preparation of a compound as claimed in claim 1 which comprises:

(A) the reaction of a compound of formula (II)

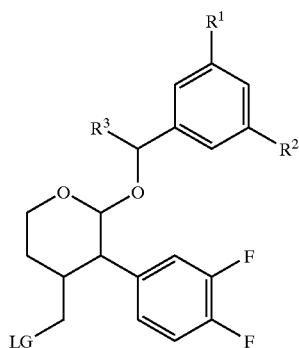

wherein LG is a suitable leaving group; with an amine of the formula

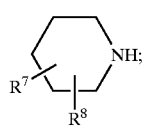

(B) the reaction of a compound of formula (IV) with a compound of formula (V)

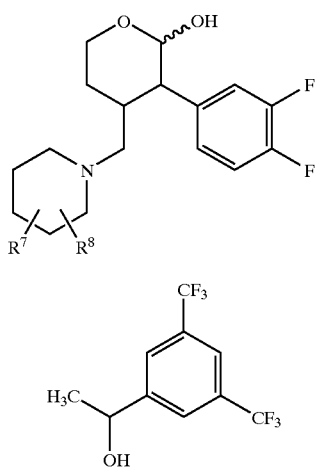

in the presence of a resin catalyst and molecular sieves; or (C) the reaction of a compound of formula (VI)

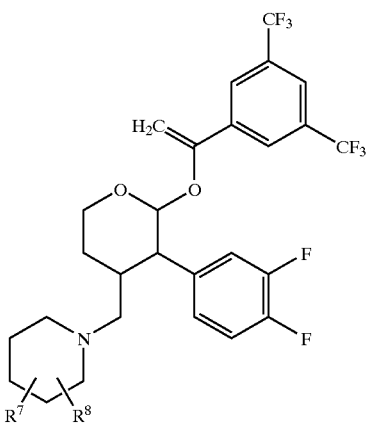

under catalytic hydrogenation conditions in a suitable solvent; or (D) reacting a compound of formula (VII)

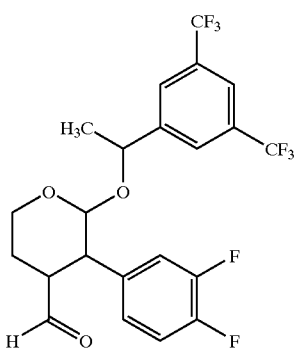

with an amine of the formula

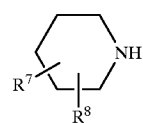

or salt thereof, in the presence of a reducing agent.

* * * * *